United States Patent [19]

Moriya et al.

[11] Patent Number: 4,639,537

[45] Date of Patent: Jan. 27, 1987

[54] CERTAIN LAEVOROTATORY P-TOLYSULFONYL OR METHANESULFONYL PROPIONIC ACID ESTER INTERMEDIATES

[75] Inventors: Koichi Moriya, Hachioji, Japan; Uwe Priesnitz, Solingen, Fed. Rep. of Germany; Hans-Jochem Riebel, Wuppertal, Fed. Rep. of Germany; Ludwig Eue, Leverkusen, Fed. Rep. of Germany; Robert R. Schmidt, Bergish-Gladbach, Fed. Rep. of Germany

[73] Assignee: Bayer Aktiengesellschaft, Leverkusen, Fed. Rep. of Germany

[21] Appl. No.: 738,105

[22] Filed: May 24, 1985

Related U.S. Application Data

[62] Division of Ser. No. 560,725, Dec. 12, 1983, Pat. No. 4,596,599.

[30] Foreign Application Priority Data

Dec. 24, 1982 [DE] Fed. Rep. of Germany ....... 3247930

[51] Int. Cl.$^4$ ................. C07C 143/38; C07C 149/32; C07C 149/40
[52] U.S. Cl. ........................................ 558/48; 558/52; 546/302; 546/301; 546/300; 560/62
[58] Field of Search ..................... 558/48, 52

[56] References Cited

U.S. PATENT DOCUMENTS 4,441,913 4/1984 Aya et al. ............................ 71/94
4,500,346 2/1985 Saito et al. ......................... 71/94

*Primary Examiner*—Alan L. Rotman
*Attorney, Agent, or Firm*—Sprung Horn Kramer & Woods

[57] ABSTRACT

New laevorotatory enantiomers of phenoxy propionic acid derivatives of the formula

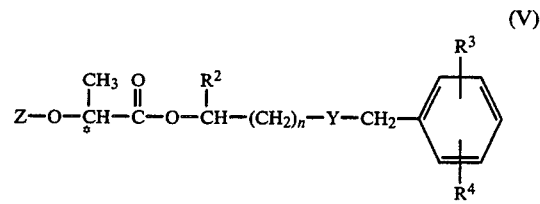

in which
$R^2$ represents a radical of the formula

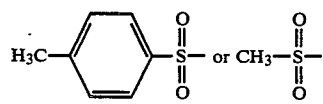

wherein
Y represents oxygen or the radical $SO_m$,
wherein
m represents 0, 1 or 2,
$R^2$ represents hydrogen or methyl,
n represents 1 or 2 and
$R^3$ and $R^4$ independently of one another represent hydrogen, halogen, alkyl with 1 to 4 carbon atoms, alkoxy with 1 to 4 carbon atoms, alkylthio with 1 to 4 carbon atoms, nitro, cyano or alkoxycarbonyl with 1 to 4 carbon atoms in the alkoxy group, and their use as intermediates for preparing herbicides.

3 Claims, No Drawings

CERTAIN LAEVOROTATORY P-TOLYSULFONYL OR METHANESULFONYL PROPIONIC ACID ESTER INTERMEDIATES

This is a division of application Ser. No. 560,725, filed Dec. 12, 1983, now U.S. Pat. No. 4,596,599 issued June 24, 1986.

The invention relates to new dextrorotatory(*) enantiomers of phenoxypropionic acid derivatives, several processes for their preparation and their use as herbicides.

(*)In this context, dextrorotatory enantiomers are in each case to be understood as meaning those optically active compounds which rotate the plane of vibration of linearly polarized light to the right.

It is already known that numerous phenoxypropionic acid derivatives have herbicidal properties (compare DE-OS (German Published Specification) No. 2,617,804 and U.S. Pat. No. 4,046,553). Thus, for example, the racemates of benzyl 2-[4-(3,5-dichloro-pyrid-2-yloxy)-phenoxy]-propionate and of (2-phenoxy)-ethyl 2-[4-(4-trifluoromethyl-phenoxy)-phenoxy]-propionate can be used for combating weeds. However, the action of these substances is not always adequate.

The new dextrorotatory enantiomers of phenoxypropionic acid derivatives of the formula

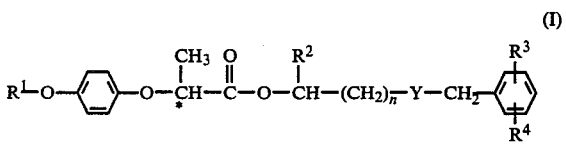

in which
R$^1$ represents a radical of the formula

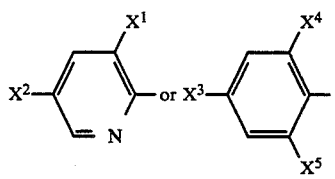

wherein
X$^1$ represents hydrogen or halogen,
X$^2$ represents halogen or trifluoromethyl,
X$^3$ represents halogen or trifluoromethyl,
X$^4$ represents hydrogen or halogen and
X$^5$ represents hydrogen or halogen,
Y represents oxygen or the radical SO$_m$,
wherein
m represents 0, 1 or 2,
R$^2$ represents hydrogen or methyl,
n represents 1 or 2 and
R$^3$ and R$^4$ independently of one another represent hydrogen, halogen, alkyl with 1 to 4 carbon atoms, alkoxy with 1 to 4 carbon atoms, alkylthio with 1 to 4 carbon atoms, nitro, cyano or alkoxycarbonyl with 1 to 4 carbon atoms in the alkoxy group,
have now been found.

It has furthermore been found that the new dextrorotatory enantiomers of phenoxypropionic acid derivatives of the formula (I) are obtained by a process in which
(a) dextrorotatory enantiomers of phenoxypropionyl chlorides of the formula

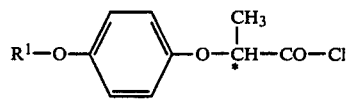

in which
R$^1$ has the abovementioned meaning,
are reacted with hydroxy compounds of the formula

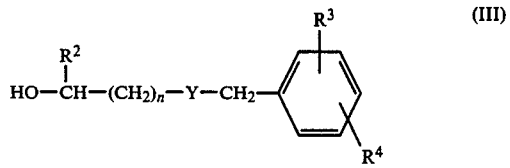

in which
R$^2$, R$^3$, R$^4$, Y and n have the abovementioned meaning,
if appropriate in the presence of an acid acceptor and if appropriate in the presence of a diluent, and, if appropriate, the product is then oxidized, or
(b) phenol derivatives of the formula

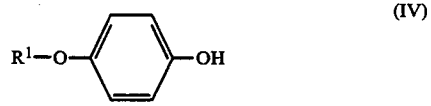

in which
R$^1$ has the abovementioned meaning,
are reacted with laevorotatory enantiomers of propionic acid derivatives of the formula

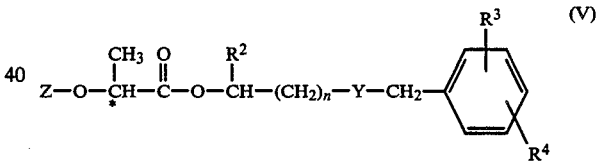

in which
R$^2$, R$^3$, R$^4$, Y and n have the abovementioned meaning and
Z represents tosyl or mesyl,
if appropriate in the presence of an acid acceptor and if appropriate in the presence of a diluent, and, if appropriate, the product is then oxidised.

Finally, it has been found that the new dextrorotatory enantiomers of phenoxypropionic acid derivatives of the formula (I) are distinguished by an outstanding herbicidal activity.

Surprisingly, the dextrorotatory enantiomers, according to the invention, of phenoxypropionic acid derivatives of the formula (I) have substantially better herbicidal properties than the racemates of benzyl 2-[4-(3,5-dichloropyrid-2-yloxy)-phenoxy]-propionate and of (2-phenoxy)-ethyl 2-[4-(4-trifluoromethylphenoxy)-phenoxy]-propionate, which are known from the prior art and are structurally similar substances of an analogous type of action.

Formula (I) provides a general definition of the compounds according to the invention. In this formula, in which the asymmetric carbon atom is labelled by (*),
R$^1$ represents a radical of the formula

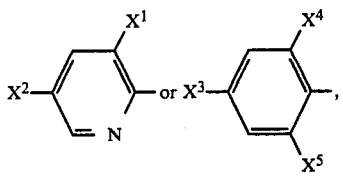
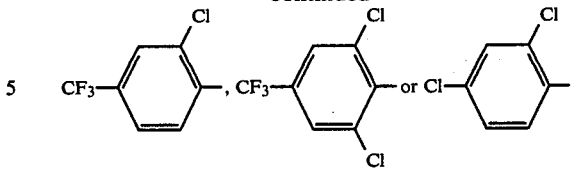

in which
X¹ represents hydrogen or chlorine,
X² represents chlorine or trifluoromethyl,
X³ represents chlorine or trifluoromethyl,
X⁴ represents hydrogen or chlorine and
X⁵ represents hydrogen or chlorine.

Y represents oxygen or the radical $SO_m$, m representing 0, 1 or 2, and $R^2$ represents hydrogen or methyl. The integer n represents 1 or 2 and the radicals $R^3$ and $R^4$ independently of one another preferably represent hydrogen, fluorine, chlorine, bromine, iodine, alkyl with 1 or 2 carbon atoms, alkoxy with 1 or 2 carbon atoms, alkylthio with 1 or 2 carbon atoms, nitro, cyano or alkoxycarbonyl with 1 or 2 carbon atoms in the alkoxy group.

Particularly preferred dextrorotatory enantiomers of phenoxypropionic acid derivatives of the formula (I) are those in which $R^1$ represents a radical of the formula

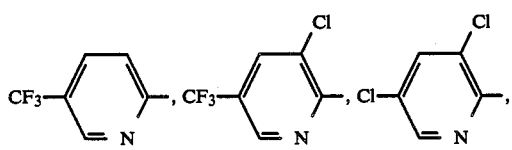

If the dextrorotatory enantiomer of 2-[4-(5-trifluoromethylpyrid-2-yloxy)-phenoxy]propionyl chloride and ethylene glycol monobenzyl ether are used as starting substances, the course of process (a) according to the invention can be represented by the following equation:

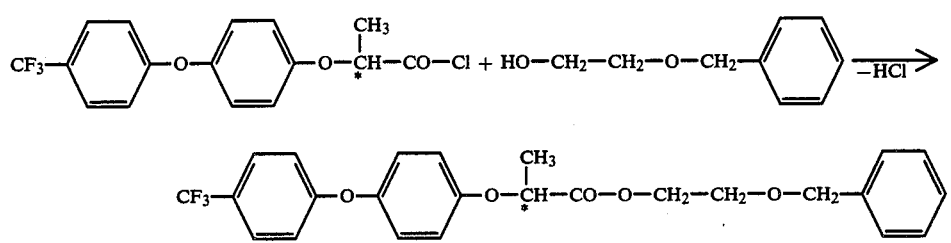

If 4-(2-chloro-4-trifluoromethylphenoxy)-phenol and the laevorotatory enantiomer of (2-benzyloxy)-ethyl 2-tosyloxy-propionate are used as starting substances, the course of process (b) according to the invention can be represented by the following equation:

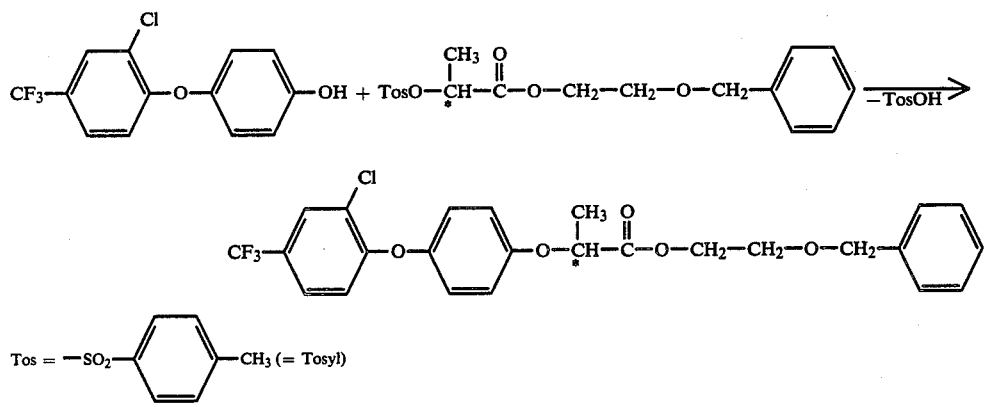

Formula (II) provides a general definition of the dextrorotatory enantiomers of phenoxypropionyl chlorides required as starting substances in process (a) according to the invention. In this formula, $R^1$ preferably represents those radicals which have already been mentioned as preferred for the substituent $R^1$ in connection with the description of the substances according to the invention.

The dextrorotatory enantiomers of the phenoxypropionyl chlorides of the formula (II) are known, or they can be prepared in a simple manner by known methods (compare DE-OS (German Published Specification) No. 2,758,002). Thus, the substances of the formula (II) can be obtained by, for example, reacting the acids on which they are based with thionyl chloride.

Formula (III) provides a general definition of the hydroxy compounds also required as starting substances in process (a) according to the invention. In this formula, $R^2$, $R^3$, $R^4$, Y and n preferably have those meanings which have already been mentioned as preferred for these radicals and for this index in connection with the description of the substances of the formula (I) according to the invention.

The hydroxy compounds of the formula (III) are known, or they can be prepared in a simple manner by known methods.

Formula (IV) provides a definition of the phenol derivatives required as starting substances in process (b) according to the invention. In this formula R¹ preferably has those meanings which have already been mentioned as preferred for this substituent in connection with the description of the substances of the formula (I) according to the invention.

The phenol derivatives of the formula (IV) are known, or they can be prepared in a simple manner by known methods (compare DE-OS (German Published Specification) No. 2,758,002, DE-OS (German Published Specification) No. 2,812,571, EP-OS (European Published Specification) No. 483 and EP-OS (European Published Specification) No. 1473).

Formula (V) provides a general definition of the laevorotatory enantiomers of propionic acid derivatives also required as starting substances in process (b) according to the invention. In this formula, $R^2$, $R^3$, $R^4$, Y and n preferably have those meanings which have already been mentioned as preferred for these substituents and for this index in connection with the description of the substances of the formula (I) according to the invention. Z represents tosyl

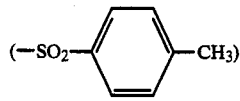

or mesyl ($-SO_2-CH_3$).

The laevorotatory enantiomers of propionic acid derivatives of the formula (V) have not yet been disclosed. However, they can be prepared in a simple manner by reacting hydroxy compounds of the formula

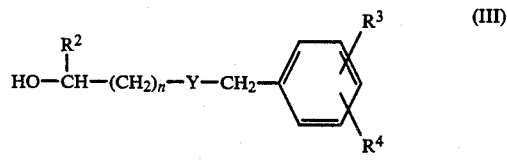

in which $R^2$, $R^3$, $R^4$, Y and n have the abovementioned meaning, with laevorotatory enantiomers of lactic acid derivatives of the formula

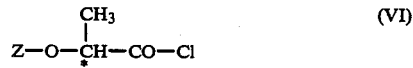

in which

Z has the abovementioned meaning, if appropriate in the presence of an acid acceptor and if appropriate in the presence of a diluent.

The hydroxy compounds of the formula (III) required as starting substances in the preparation of the laevorotatory enantiomers of propionic acid derivatives of the formula (V) have already been treated in connection with the description of process (a) according to the invention. The laevorotatory enantiomers of lactic acid derivatives of the formula (VI) also required as reaction components in the reaction for the synthesis of compounds of the formula (V) are known, or they can be prepared in a simple manner by known methods.

Processes (a) and (b) according to the invention and the process for the preparation of substances of the formula (V) are preferably carried out using diluents.

Possible diluents for this are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and dimethylsulphoxide, tetramethylenesulphone and hexamethylphosphoric acid triamide.

Acid acceptors which can be used both in processes (a) and (b) according to the invention and in the process for the preparation of compounds of the formula (V) are all the acid-binding agents which can usually be employed for such reactions. Preferred acid acceptors are alkali metal hydroxides and alkaline earth metal hydroxides and oxides, such as, for example, sodium and potassium hydroxide, calcium hydroxide and calcium oxide, alkali metal carbonates and alcoholates, such as sodium and potassium carbonate and sodium and potassium methylate or ethylate, and furthermore aliphatic, aromatic or heterocyclic amines, for example triethylamine, trimethylamine, dimethylaniline, dimethylbenzylamine, 1,5-diazabicyclo[4,3,0]non-5-ene (DBN), 1,8-diazabicyclo[5,4,0]undec-7-ene (DBU) and pyridine.

The reaction temperatures can be varied within a substantial range both in processes (a) and (b) according to the invention and in the process for the preparation of the compounds of the formula (V). In general, the reaction is in each case carried out at temperatures between $-20°$ C. and $+160°$ C., preferably between $-10°$ C. and $+100°$ C.

Processes (a) and (b) according to the invention and also the process for the preparation of the compounds of the formula (V) are in general carried out under normal pressure. However, it is also possible to carry out the processes under increased or reduced pressure.

For the preparation of those compounds of the formula (I) in which Y represents $SO_m$ and m represents 1 or 2, those substances of the formula (I) in which Y represents sulphur are oxidized, by customary methods, with the particular amounts required, or with an excess, of oxidizing agent, if appropriate in the presence of a catalyst and in the presence of a diluent.

Oxidized agents which can be used here are all the customary oxygen-donating oxidizing agents. Preferred agents are hydrogen peroxide, peracetic acid and m-chloroperbenzoic acid.

Possible diluents in carrying out this oxidation are all the organic solvents which can usually be employed for such oxidations. Glacial acetic acid or methylene chloride can preferably be used.

Catalysts which can be used in this oxidation are all the reaction accelerators which can customarily be employed for such oxidations. Formic acid and sulphuric acid can preferably be used.

The temperatures can be varied within a certain range for the oxidation. In general, the oxidation is carried out between −20° C. and +50° C., preferably between 0° C. and +40° C.

In carrying out the oxidation, the starting compound of the formula (I) is in general reacted with the particular calculated amount or with a slight excess of oxidizing agent. Working up is in each case effected by customary methods.

For carrying out processes (a) and (b) according to the invention and the process for the preparation of the compounds of the formula (V), the particular starting substances required are in general employed in approximately equimolar amounts. However, it is also possible to use one or both of the particular components employed in a larger excess. The reactions are in general carried out in a suitable diluent in the presence of an acid acceptor, and the reaction mixture is stirred at the particular temperature required for several hours. Working up is in each case effected by customary processes. In general, a procedure is followed in which water is added to the reaction mixture and the mixture is extracted with an organic solvent of low water-miscibility and the combined organic phases are dried and concentrated by stripping off the solvent.

Some of the new compounds are obtained in the form of oils, some of which cannot be distilled without decomposition, but can be freed from the last volatile constituents by so-called "incipient distillation", that is to say by prolonged heating to moderately elevated temperatures under reduced pressure, and can be purified in this manner.

The active compounds according to the invention can be used as defoliants, desiccants, agents for destroying broad-leaved plants and especially as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connction with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassicia, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Spenoclea, Dactyloctenium, Agrostis, Alopecurus and Apera.

Monocotyledon cultures and the genera: Oryza, Zea; Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds cab be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions and mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixing being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzthiazolyl)-N,N'-dimethyl-urea, for combating weeds in cereals; 4-amino-3-methyl-6-phenyl-1,2,4-triazin-5(4H)-one, for combating weeds in sugar beet, and 4-amino-6-(1,1-dimethylethyl)-3-methylthio-1,2,4-triazin-5(4H)-one, for combating weeds in soybean. Surprisingly, some mixtures also display a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the examples which follow.

PREPARATION EXAMPLES

Example 1

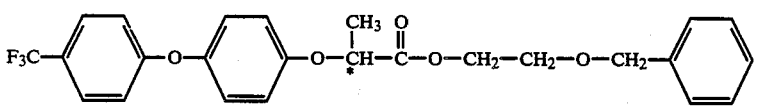

5 g (0.042 mol) of thionyl chloride were added dropwise to a solution of 7 g (0.021 mol) of the dextrorotatory enantiomer of 2-[4-(4-trifluoromethyl-phenoxy)-phenoxy]-propionic acid in 80 ml of toluene, while stirring, and the reaction mixture was then heated under reflux for 2 hours. Thereafter, the reaction mixture was concentrated by stripping off the solvent and the residue was added to a solution of 2.7 g (0.017 mol) of glycol monobenzyl ether and 3 g (0.03 mol) of triethylamine in 50 ml of toluene at 0° C. to 5° C., while stirring. Stirring was continued at room temperature for 16 hours and the reaction mixture was then worked up by adding water and drying the combined organic phases and concentrating them under reduced pressure. The residue which remained was freed from traces of volatile constituents by warming slightly under a high vacuum. 6.2 g (62.6% of theory) of the dextrorotatory enantiomer of (2-benzyloxy)-ethyl 2-[4-(4-trifluoromethyl-phenoxy)-phenoxy]-propionate were obtained in this manner.

Optical rotation: $[\alpha]_D^{24} = +4.2°$ (1 molar solution in chloroform; cell length=10 cm).

Example 2

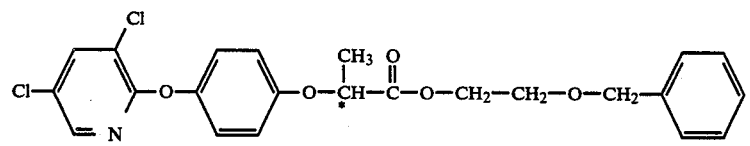

A mixture of 25.6 g (0.1 mol) of 4-(3,5-dichloropyrid-2-yloxy)-phenol, 37.8 g (0.1 mol) of the laevorotatory enantiomer of (2-benzyloxy)-ethyl 2-tosyloxypropionate and 16.6 g (0.12 mol) of potassium carbonate in 200 ml of acetonitrile was heated under reflux for 14 hours. The reaction mixture was then cooled to room temperature and 400 ml of water were added. The mixture was extracted with two 200 ml portions of toluene. The combined organic phases were dried over sodium sulphate and concentrated by stripping off the solvent under reduced pressure. The residue which remained was freed from traces of volatile constituents by warming slightly under a high vacuum. 28 g (60% of theory) of the dextrorotatory enantiomer of (2-benzyloxy)-ethyl 2-[4-(3,5-dichloropyrid-2-yloxy)-phenoxy]-propionate were obtained in this manner.

Optical rotation: $[\alpha]_D^{24} = +10.2°$ (1 molar solution in chloroform; cell length=10 cm).

Preparation of the starting substance

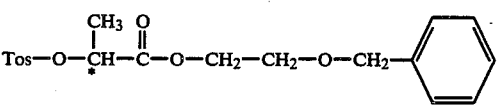

(V-1)

5.25 g (0.02 mol) of the laevorotatory enantiomer of lactyl chloride tosylate were added to a mixture of 3.32 g (0.02 mol) of glycol monobenzyl ether, 2 g (0.02 mol) of triethylamine and 50 ml of toluene at 20° C., while stirring. Stirring was continued at 70° C. for 14 hours and the reaction mixture was then worked up by adding 100 ml of water, extracting the mixture several times with toluene and drying the combined organic phases and concentrating them by stripping off the solvent under reduced pressure. 6.3 g (80.5% of theory) of the laevorotatory enantiomer of (2-benzyloxy)-ethyl 2-tosyloxy-propionate were obtained in this manner.

Optical rotation: $[\alpha]_D^{24} = -10.2°$ (1 molar solution in chloroform; cell length = 10 cm).

The substances of the formula (I) listed by way of their formulae in the table which follows were also prepared by the methods described in Examples 1 and 2.

TABLE 1

$$R^1-O-\underset{}{\bigcirc}-O-\overset{CH_3}{\underset{*}{CH}}-\overset{O}{\overset{\|}{C}}-O-\overset{R^2}{\underset{}{CH}}-(CH_2)_n-Y-CH_2-\underset{R^4}{\overset{R^3}{\bigcirc}} \quad (I)$$

| Example No. | R¹ | R² | n | Y | R³ | R⁴ | Optical rotation $[\alpha]_D^{24}$ |
|---|---|---|---|---|---|---|---|
| 3 | 3,5-Cl₂-pyridin-2-yl | H | 1 | O | 2-F | H | +7.9 |
| 4 | 3,5-Cl₂-pyridin-2-yl | H | 1 | O | 4-Cl | H | +8.7 |
| 5 | 5-CF₃-pyridin-2-yl | H | 1 | O | H | H | +10.0 |
| 6 | 5-CF₃-pyridin-2-yl | H | 1 | O | 2-F | H | +9.1 |
| 7 | 5-CF₃-pyridin-2-yl | H | 1 | O | 4-Cl | H | +9.9 |
| 8 | 5-CF₃-pyridin-2-yl | H | 2 | O | H | H | +10.3 |
| 9 | 5-CF₃-pyridin-2-yl | H | 1 | S | H | H | +14.1 |
| 10 | 3,5-Cl₂-pyridin-2-yl | CH₃ | 1 | O | H | H | +3.1 |
| 11 | 3,5-Cl₂-pyridin-2-yl | H | 1 | S | H | H | +10.5 |

The substances of the formula (V) listed by way of their formulae in the table which follows were also synthesized by the method of the preparation of the compound (V-1) described in Example 2.

TABLE 2

$$Z-O-\overset{CH_3}{\underset{*}{CH}}-\overset{O}{\overset{\|}{C}}-O-\overset{R^2}{\underset{}{CH}}-(CH_2)_n-Y-CH_2-\underset{R^4}{\overset{R^3}{\bigcirc}} \quad (V)$$

| Example No. | Z | R² | n | Y | R³ | R⁴ | Optical rotation $[\alpha]_D^{24}$ |
|---|---|---|---|---|---|---|---|
| (V-2) | Tos | H | 1 | O | 2-F | H | −9.7 |
| (V-3) | Tos | H | 2 | O | H | H | −10.3 |
| (V-4) | Tos | CH₃ | 1 | O | H | H | −4.1 |
| (V-5) | Tos | H | 1 | O | 4-Cl | H | −7.6 |
| (V-6) | Tos | H | 1 | S | H | H | −10.9 |

Example 12

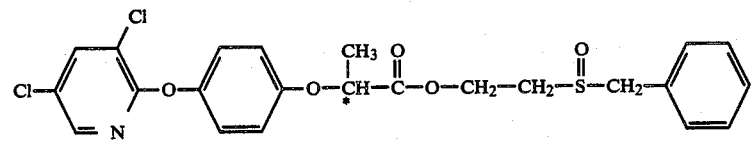

5.7 g of 30% strength aqueous hydrogen peroxide solution were added dropwise to a solution of 24 g (0.05 mol) of the dextrorotatory enantiomer of (2-benzylthio)-ethyl 2-[4-(3,5-dichloropyrid-2-yloxy)-phenoxy]-propionate in 100 ml of glacial acetic acid at +10° C., while stirring. The reaction mixture was stirred at 20° C. for 10 hours and 10 ml of aqueous potassium bisulphite solution and 200 ml of water were then added in succession. For further working up, the reaction mixture was extracted with two 100 ml portions of methylene chloride. The combined organic phases were washed with 50 ml of saturated aqueous potassium carbonate solution and then with two 100 ml portions of water. After drying and stripping off the solvent under reduced pressure, 19 g (76% of theory) of the dextrorotatory enantiomer of (2-benzylsulphinyl)-ethyl 2-[4-(3,5-dichloro-pyrid-2-yloxy)-phenoxy]-propionate were obtained in the form of colourless crystals of melting point 112° C.

Optical rotation: $[\alpha]_D^{24} = +12.2°$.

Example 13

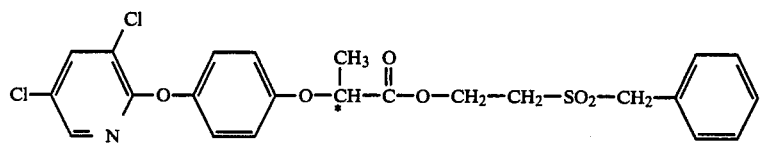

5 g (0.11 mol) of formic acid were first added dropwise, while stirring, to a solution of 24 g (0.05 mol) of the dextrorotatory enantiomer of (2-benzylthio)-ethyl 2-[4-(3,5-dichloropyrid-2-yloxy)-phenoxy]-propionate in 150 ml of methylene chloride at 20° C., followed by 0.5 ml of sulphuric acid at 20° C. and then 16.5 g of 30% strength aqueous hydrogen peroxide solution at 10°–20° C. The reaction mixture was stirred at 20° C. for 10 hours and 10 ml of aqueous potassium bisulphite solution and 200 ml of water were then added in succession. For further working up, the reaction mixture was extracted with two 100 ml portions of methylene chloride. The combined organic phases were washed with 50 ml of saturated aqueous potassium carbonate solution and then with two 100 ml portions of water. After drying and stripping off the solvent under reduced pressure, 21 g (81% of theory) of the dextrorotatory enantiomer of (2-benzylsulphonyl)-ethyl 2-[4-(3,5-dichloropyrid-2-yloxy)-phenoxy]-propionate were obtained in the form of a yellow oil of refractive index $n_D^{20}$ 1.5807.

Optical rotation: $[\alpha]_D^{24} = +15.1°$.

Example A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:
0% = no action (like untreated control)
100% = total destruction In this test, the active compounds according to the invention exhibit a very good activity.

Example B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:
0% = no action (like untreated control)
100% = total destruction In this test, active compounds 2, 4, 5 and 7–9 according to the invention exhibit a very good activity.

TABLE

| | Post-emergence test Greenhouse | | | |
|---|---|---|---|---|
| | Amount of active | % damage or % action | | |
| Active compound | compound kg/ha | Sugar-beet | Soy-bean | Echino-chloa | Setaria |
| (2) | 0.25 | 0 | 0 | 100 | 100 |
| (4) | 0.25 | 0 | 0 | 100 | 100 |
| (5) | 0.25 | 0 | 0 | 100 | 95 |
| (7) | 0.25 | 0 | 0 | 100 | 99 |
| (8) | 0.25 | 0 | 0 | 100 | 99 |
| (9) | 0.25 | 0 | 25 | 99 | 99 |

What is claimed is:

1. A laevorotatory enantiomer of the formula

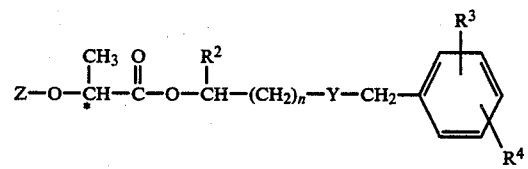

in which
  Z represents tosyl or mesyl,
  Y represents oxygen or the radical $SO_m$,
wherein
  m represents 0, 1 or 2,
  $R^2$ represents hydrogen or methyl,
  n represents 1 or 2 and
  $R^3$ and $R^4$ independently of one another represent hydrogen, halogen, alkyl with 1 to 4 carbon atoms, alkoxy with 1 to 4 carbon atoms, nitro, cyano or alkoxycarbonyl with 1 to 4 carbon atoms in the alkoxy group.

2. A laevorotatory enantiomer according to claim 1, wherein Y represents oxygen.

3. A laevorotatory enantiomer according to claim 1, wherein Y represents $SO_m$.

* * * * *